(12) United States Patent
Kesling et al.

(10) Patent No.: US 7,264,468 B1
(45) Date of Patent: Sep. 4, 2007

(54) EDGEWISE ORTHODONTIC BRACKET FOR CAPTURING LOST TORQUE

(76) Inventors: Peter C. Kesling, 611 W. 250 South, LaPorte, IN (US) 46350; Richard C. Parkhouse, Bryn Tirion, Penmaen Park, Llanfairfechan, Gwynedd, LL33 0RN Wales (GB); Christopher K. Kesling, Green Acres, LaPorte, IN (US) 46350

( * ) Notice: Subject to any disclaimer, the term of this patent is extended or adjusted under 35 U.S.C. 154(b) by 251 days.

(21) Appl. No.: 11/027,043

(22) Filed: Dec. 30, 2004

(51) Int. Cl.
*A61C 7/12* (2006.01)
(52) U.S. Cl. .............................. 433/8; 433/10
(58) Field of Classification Search ............... 433/8–18
See application file for complete search history.

(56) References Cited

U.S. PATENT DOCUMENTS

| | | | |
|---|---|---|---|
| 4,415,330 A * | 11/1983 | Daisley et al. | 433/16 |
| 4,877,398 A | 10/1989 | Kesling | |
| 5,125,832 A | 6/1992 | Kesling | |
| 5,820,370 A * | 10/1998 | Allesee et al. | 433/8 |
| 6,682,345 B2 * | 1/2004 | Kesling et al. | 433/8 |
| 6,685,468 B1 | 2/2004 | Kesling | |
| 2003/0180678 A1 * | 9/2003 | Kesling et al. | 433/8 |
| 2006/0019211 A1 * | 1/2006 | Ricketts et al. | 433/8 |

OTHER PUBLICATIONS

Angle, E.H., The Lastest and Best in Orthodontic Mechnism, Dental Cosmos 1928; 70:1143-1158.
Andrews, L.F., The Six Keys to Normal Occlusion, Amercian Journal of Orthodontics 1972; 62:296.
McLaughlin, R.P., Bennett, J.C., Trevisi, H.J., Systemized Orthodontic Treatment Mechanics, 2001, pp. 17, 32-34.
Kapur-Wadhwa, R., Physical and Mechanical Properties Affecting Torque Control, Journal of Clinical Orthodontics 2004; 38:335-340.

* cited by examiner

*Primary Examiner*—Cris Rodriguez
*Assistant Examiner*—Patrick J. Kilkenny
(74) *Attorney, Agent, or Firm*—Lloyd L. Zickert

(57) ABSTRACT

An edgewise orthodontic bracket for use in an edgewise or straight-wire technique having a standard horizontally opening rectangular archwire slot and a mesiodistally extending tunnel or lumen separate from and vertically angled to the archwire slot for receiving a relatively small flexible wire during the use of an undersize rectangular archwire in the archwire slot to apply a force to the bracket for capturing lost torque.

22 Claims, 3 Drawing Sheets

EDGEWISE ORTHODONTIC BRACKET FOR CAPTURING LOST TORQUE

This invention relates in general to an edgewise orthodontic bracket having a rectangular archwire slot for receiving a rectangular archwire and a tunnel for receiving a small flexible wire to apply forces to the bracket and eliminate the play or tolerance between a vertically undersize archwire and the archwire slot, and more particularly to a new and improved orthodontic edgewise bracket for capturing lost torque and achieving more accurate results in the final positioning of teeth.

BACKGROUND OF THE INVENTION

When Dr. Edward Angle first introduced the brackets and archwires for the edgewise mechanism in 1925, the archwires were made of gold and the brackets from a solid block of metal. Dr. Angle originally claimed his edgewise archwire was " . . . exactly 0.022 inch in thickness and 0.028 inch in width, and it most accurately fits the slots in brackets." (Angle, E. H., The latest and best in orthodontic mechanism. Dental Cosmos 1928;70:1143–1158.) Dr. Angle's use of the term "accurately" leaves the reader with the assumption that the slot is also 0.022 inch. Of course, if this were the case, it would have been nearly impossible to insert the wires into the slots.

Accordingly, even though the same sizes are listed for slots and wires, the slots must be a little larger and/or the wires slightly smaller. It has become accepted procedure to manufacture archwire slots oversize vertically from 0.001 inch to 0.002 inch and the rectangular archwires 0.0005 inch undersize. Therefore, all edgewise archwires are undersize vertically as compared to their respective archwire slots.

The differences between the various listed and advertised sizes, and the actual rectangular wire and slot sizes, and the resulting vertical tolerances are illustrated in the following chart:

| Wire Size (Listed) | Wire Size (Actual) | Slot Size (Listed) | Slot Size (Actual) | Vertical Tolerance |
| --- | --- | --- | --- | --- |
| 0.018" × 0.025" | 0.0178" × 0.0251" | 0.018" | 0.0189" | 0.0011" |
| 0.019" × 0.025" | 0.0188" × 0.0247" | 0.019" (none) | 0 | 0 |
| 0.0215" × 0.028" | 0.0214" × 0.0279" | 0.022" | 0.0231" | 0.0017" |

This amount of tolerance or play is necessary to facilitate the placement and removal of archwires. The resultant lack of exact axial control with the edgewise mechanism has been accepted as a "fact of life" in orthodontics for the past eighty years.

The following definitions of dental directional terms will be referred to clarify the understanding of the invention:
Mesial—toward the front of the dental arch
Buccal/labial—toward the cheek or lip
Palatal/lingual—toward the palate or tongue
Tip—inclination of bracket or tooth in mesial-distal direction
Torque—inclination of bracket or tooth in labial-lingual direction
Occlusal/incisal—toward the biting surface of tooth
Gingival—toward the gums.

However, this play can be eliminated by the orthodontist when placing small bends in the archwire to achieve desired final degrees of tip or torque. By placing vertical steps (second order bends) in the wire on either side of the bracket to tip the tooth mesially or distally, the wire is angled in relation to the level slot and makes contact with diagonally opposed ends of the slot. Of course, the wire must actually be overbent to overcome the vertical play and deliver the desired degree of tooth tip. This, of course, requires much skill and thought on the part of the orthodontist.

To achieve the desired degree of torque the orthodontist must twist the rectangular archwire about its long axis (third order adjustment). These bends are time-consuming and the flexing required to place the bent wires into the slots can be very uncomfortable for the patient. Such wires often require the use of special seating tools or torquing keys to insert them into the slots.

This was the recommended practice in orthodontics when the edgewise appliance was originally introduced by Dr. Angle in the 1920's and continued by Dr. Charles Tweed and others through the 1960's.

In the early 1970's the idea of preadjusted archwire slots became popular, as advocated by Dr. Lawrence Andrews (Andrews, L. F., The six keys to normal occlusion. Am J Orthod 1972;62:296.) The concept is to angle the archwire slots both mesiodistally (for desired tip) and buccolingually (for desired torque) so that "straight" archwires can be used with no need for bending by the orthodontist. The popular term for this concept is the straight-wire appliance because theoretically there are no individual bends required for each tooth. Prescriptions of differing degrees are provided to treat various types of patients.

When referring to a "prescription" herein, it will be understood to mean a system to be followed by an orthodontist when treating a patient to obtain a desired end result. Such a system would use a series of brackets at least some of which would have built in degrees of tip and torque for each of the teeth on which those brackets are to be mounted.

However, this created another problem. In the absence of the overbending described above, the vertical play or tolerance between the wire and the slot and its associated lack of torque and tip control became more significant. As shown below, the play (degrees of lost control) is much greater in regard to torque than tip.

When using straight "full-size" edgewise archwires in their respective slots, the following torque and tip play is produced:

| Wire Size (Listed) | Slot Size (Listed) | Torque Play | Tip-Play 0.075" Wide | Tip-Play 0.160" Wide |
| --- | --- | --- | --- | --- |
| 0.018" × 0.025" | 0.018" | 2.6 Degrees | 1.2 Degrees | 0.4 Degrees |
| 0.0215" × 0.028" | 0.022" | 4.0 Degrees | 1.8 Degrees | 0.6 Degrees |

Actually, the range of torque and tip play is double the degrees listed above as the tooth/bracket can rotate back and forth about the archwire in two directions.

Accordingly, the necessary slot and archwire size tolerances required to facilitate placement of archwires in the bracket slots results in lost tip and torque control. To compensate for lost torque control due to vertical tolerances between the archwire and a conventional edgewise slot, the straight wire torque prescription (angulation) can be "over done." In other words, when −12 degrees of palatal root torque is desired for the maxillary central incisors and there is 4 degrees of play when using a "full-size" 0.0215"×0.028" archwire in a 0.022" slot, the torque prescription in the base of the bracket or the slot is increased to −16 degrees. Theoretically then, when using a flat, full-size archwire, the maxillary central incisors will be moved to, or held in axial positions of −12 degrees of palatal root torque.

In 1986 Peter C. Kesling invented the Tip-Edge® bracket as disclosed in U.S. Pat. No. 4,877,398, and developed the Tip-Edge® technique for orthodontically treating a patient. This Tip-Edge® bracket includes a unique archwire slot that initially permits up to 30 degrees of tipping and finally provides 100 percent of both torque and tip control. Tip-Edge® is a registered trademark to TP Orthodontics, Inc., of Westville, Ind.

Unlike a conventional edgewise slot with directly opposed parallel walls, there is no control of tip or torque without an uprighting spring or the threading of an auxiliary wire through a tunnel, as disclosed in U.S. Pat. No. 6,682,345. Because the unique Tip-Edge slot does not bind on the archwire when sliding teeth/brackets mesially or distally, there is no need to use undersize archwires in the slot to facilitate tooth movement.

Dr. Kesling also disclosed in 1997 (Kesling PC. Vertical slots—expanding the versatility of edgewise brackets. Video April 1997) that through the power of a mesiodistal uprighting spring, a bracket with a conventional edgewise slot could be rotated in conjunction with a full size rectangular archwire to provide 100 percent torque control. However, because of a general dislike for uprighting springs that are difficult to use, unsightly, uncomfortable and unhygienic, few orthodontists have attempted to capture lost torque in this manner. Such a procedure has evidently never been suggested in the literature.

In recent years this problem of lost torque due to the vertical tolerances between the wire and a conventional edgewise archwire slot has been exacerbated by the practice of using substantially undersize rectangular archwires in the straight-wire technique. Archwires of 0.019"×0.025" are employed in 0.022" slots. The increase in tolerance is necessary to facilitate bodily sliding the brackets/teeth along the wire. It also aids archwire engagement and reduces patient discomfort.

However, no such use of substantially undersize archwires has proved necessary when using Tip-Edge brackets because as mentioned before the Tip-Edge slot does not bind on the archwire. It, in effect, increases in size vertically as brackets/teeth are slid along the full-size wire.

The use of 0.019×0.025 archwires in 0.022 slots results in the following ranges of torque and tip play:

The increase in lack of tip and torque control caused by the ranges of play above has been clearly recognized in the leading straight-wire textbook and reported in the literature (McLaughlin, R. P., Bennett, J. C., Trevisi, H. J. Systemized orthodontic treatment mechanics. Edinburgh, Mosby, 2001. Kapur-Wadhwa, R. Physical and mechanical properties affecting torque control. J Clin Orthod 2004;38:335–340.)

SUMMARY OF THE INVENTION

By using a relatively flexible wire threaded through a tunnel inclined to the archwire slot in a bracket having a conventional archwire slot, wherein with an undersize rectangular archwire, as in the present invention, it is now possible to capture lost torque. It will be understood that "undersize rectangular archwire" as used herein means an archwire having a height or vertical dimension of at least 0.001 inch less than the height or vertical dimension of the archwire slot.

The bracket/tooth is power rotated in one, predetermined direction, mesially or distally, by a flexible wire until diagonally opposed ends of the archwire slot strike the upper and lower surfaces of the undersized rectangular archwire.

Since it is only necessary to tip the tooth in one direction, the degree of over tip achieved is just one-half the full range of tip play. Therefore, when using a 0.160" wide bracket with a 0.022" archwire slot in conjunction with a 0.019"× 0.025" archwire, the bracket is only over tipped 1.6 degrees (one-half the 3.2 degree range of tipping).

This small amount of over tipping is not necessarily objectionable. In fact, it is a degree of over treatment which is often desired to help offset a slight relapse that normally occurs when the appliances (braces) are removed. It is inconsequential when compared to being able to control a 21+degree range of torque play to achieve 100 percent of desired labial or lingual root torque without having to carefully make numerous bends in the archwire.

However, the invention can be practiced with three types of brackets all having vertically inclined deep tunnels or lumens to accept highly flexible uprighting wires as follows:

A. A conventional edgewise bracket for use in the straight wire technique would have the archwire slot parallel to the top and bottom of the bracket with a tip prescription designated at its actual value. Practicing the invention with an undersize rectangular archwire would result in overtipping.

B. Conventional appearing (i.e. slot parallel to the upper and lower bracket surfaces), straight-wire preadjusted brackets can be used to practice the invention without over tipping by misrepresenting their tip prescription angulations. When using 0.160" wide brackets with 0.022" archwire slots and 0.019"×0.025" archwires, the following actual tip angles can be built into the brackets.

| Listed Wire Size | Listed Slot Size | Actual | Actual | Actual Vertical Tolerance | Range of Torque Play | Range of Tip-Play | |
|---|---|---|---|---|---|---|---|
| | | | | | | 0.160" Wide Brackets | 0.075" Wide Brackets |
| 0.019" × 0.025" | 0.022" | 0.0188" × 0.0247" | 0.0231" | 0.043" | 21.6 Degrees | 3.2 Degrees | 9 Degrees |

| | Desired & Designated Tip Angle | Actual Tip Angle In Bracket | Tip angle achieved when power rotated in conjunction with 0.019" × 0.025" archwire to achieve 100 Percent of torque |
|---|---|---|---|
| Upper Central Incisor | 5° | 3.4° | 5° |
| Upper Lateral Incisor | 9° | 7.4° | 9° |
| Upper Canine | 11° | 9.4° | 11° |
| Upper Premolar | 2° | 0.4° | 2° |
| Lower Central Incisor | 2° | 0.4° | 2° |
| Lower Lateral Incisor | 2° | 0.4° | 2° |
| Lower Canine | 5° | 3.4° | 5° |
| Lower Premolar | 2° | 0.4° | 2° |

C. The bracket can take the shape associated with the predetermined tip angulation and the archwire slot is offset at an inclination (1.6 degrees when the bracket is 0.160" wide, the archwire slot is 0.022" and the archwire is 0.019"×0.025"). The ends of the slot will therefore bottom out on the incisal and gingival surfaces of the undersized rectangular archwire with the upper and lower surfaces of the bracket parallel with the archwire and the tooth/bracket at both the desired tip and torque angles.

The present invention relates to power uprighting a conventional edgewise bracket mesiodistally by a highly flexible wire threaded through an inclined tunnel to achieve one hundred percent of the torque value built into the archwire slot when the diagonally opposite ends of the slot bottom out on the upper and lower surfaces of an undersized rectangular archwire.

With only a few thousandths of inches of tolerance between archwires and slots the teeth will only tip 3 to 5 degrees and remain essentially upright while being retracted bodily rather than by free crown tipping. This compares to tipping up to 60 degrees as is the case with ribbon arch brackets and up to 30 degrees with Tip-Edge® brackets.

Heretofore, as disclosed in U.S. Pat. No. 6,682,345, as mentioned above, it has been known to provide brackets with a Tip-Edge® slot for performing the Tip-Edge® technique that included tunnels or lumens for receiving a flexible wire to produce an uprighting function, and eliminate the need for uprighting springs. However, with Tip-Edge® brackets the primary purpose or function of tunnels and resilient auxiliary wires is to upright tipped teeth to desired tip angulations. Full-size round or rectangular archwires are used, and any changes in torque angulations are secondary.

With the present invention undersized rectangular wires are always employed. The teeth are limited from tipping to undesired inclinations by the parallel upper and lower surfaces of the edgewise archwire slots. The primary purpose of the resilient wires through the mesiodistal directed lumens or tunnels is to capture lost torque by bottoming the ends of the rectangular archwire slots against the upper and lower surfaces of the undersize rectangular archwires. Resultant changes in tip angulations are secondary and relatively minor.

Another advantage of capturing lost torque by reducing the vertical tolerance through powered tunnel tipping rather than overbending (twisting) the archwire or over-pretorquing the archwire slot is that the resultant torque forces are lighter, more uniform, and longer lasting, resulting in increased patient comfort.

To increase the force delivered at the ends of the archwire slot, the tunnel can be longer than the slot itself. For example, by shortening the archwire slot to half the length of the tunnel, the mechanical advantage of the system in terms of the force transmitted from the flexed uprighting wire, incident upon the archwire at opposite ends of the archwire slot, would be magnified. Thus, the rate of torquing and recapture of lost torque will be increased. It will be appreciated that the length of the tunnel is preferably at least equal to the length of the archwire slot, but that it may be longer or shorter.

With the present invention, there is no need to exaggerate preadjusted torque values in slots or to bend archwires. This in turn facilitates archwire engagement of archwires in the slots and lessens initial force values and discomfort to the patients.

The use of an undersize archwire in a conventional edgewise archwire slot permits a reduction of 1.6 to 4.5 degrees in the mesial crown tip angle during retraction. This facilitates bodily tooth movement. Once the teeth are retracted and/or spaces closed, the teeth can be uprighted to the desired final degrees of crown tip by forces from a highly flexible wire threaded through the generally angled tunnels in two or more adjacent brackets.

By the use of a unique sized archwire heretofore not common in the practice of orthodontics, it will be possible to further increase the efficiency of the torquing process. The new wire is 0.019" vertically and 0.028" horizontally. The increase in archwire width offers wider surfaces to act against the upper and lower surfaces of the archwire slot, which facilitates the generation of the secondary torquing couple. The result will be about an 11 percent increase in speed of recovery of lost torque, compared with the use of a conventional 0.019"×0.025" archwire, thereby expediting the capture of lost torque.

However, since the unique 0.019"×0.028" archwire remains undersize vertically, when used in a 0.022" archwire slot, bodily movement of teeth by free sliding of the brackets along the wire is unimpaired, as is ease of engagement and patient comfort.

It is therefore an object of the present invention is to provide a new and improved edgewise orthodontic bracket that provides means of capturing "lost torque" from an undersize rectangular archwire in an edgewise archwire slot by threading a highly flexible uprighting wire through an angular tunnel.

Another object of the present invention is to achieve the desired degrees of final crown tip and root torque when using an undersize archwire in an edgewise bracket without having to make bends in the archwire.

A further object of the present invention is to allow a reduction in the mesial crown tip angle of a tooth while practicing a straight-wire technique in an edgewise bracket to lessen the strain on anchorage when retracting said tooth on an undersize archwire and still be able to achieve at the end of treatment the desired mesiodistal (tip) inclination without using individual uprighting springs.

A still further object of the present invention is to permit the use of undersize archwires in edgewise straight-wire brackets to lessen force levels and reduce friction while bodily sliding the brackets/teeth along the archwires without compromising control of final desired inclinations of the teeth.

Another object of the present invention is to permit the use of mesiodistal uprighting forces in conjunction with an undersize archwire in an edgewise bracket with an edgewise archwire slot without over uprighting the tooth.

Other objects, features and advantages of the invention will be apparent from the following detailed disclosure, taken in conjunction with the accompanying sheets of drawings, wherein like reference numerals refer to like parts.

DESCRIPTION OF THE INVENTION

Figure 1:
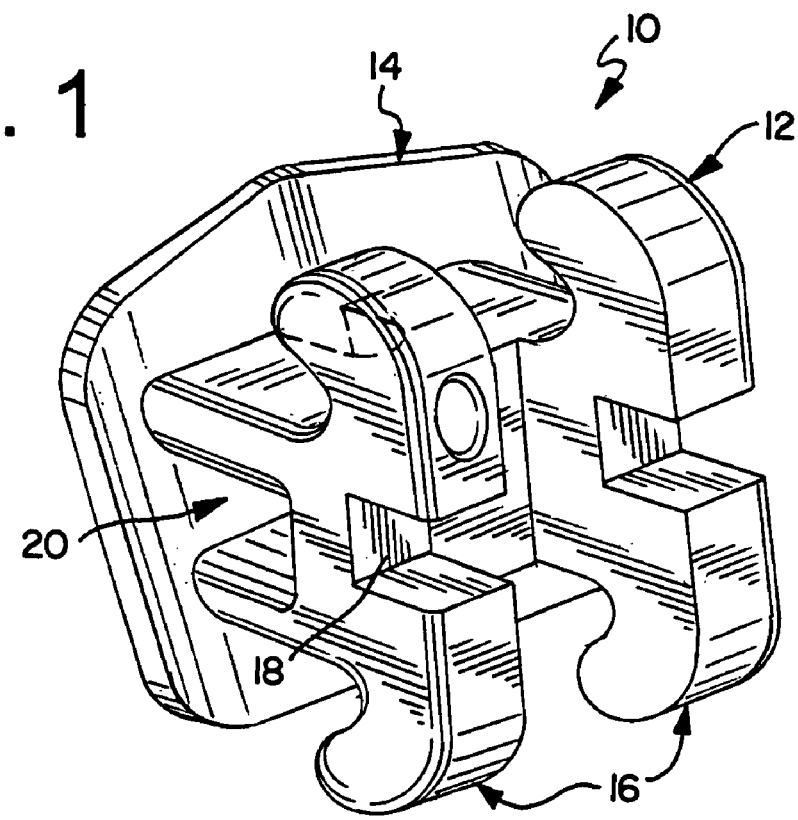
FIG. 1 is a perspective view of an edgewise bracket according to the invention and for use on the upper right central incisor tooth.

The improved edgewise bracket of the present invention solves the problem of capturing lost torque created in edgewise brackets during the final stages of orthodontic treatment due to the inevitable vertical tolerances necessary between the archwire slots and archwires themselves necessitated to permit the insertion of the wires. The invention avoids the heretofore often used wire-bending techniques to capture the lost torque by providing tunnels or lumens in the brackets angularly disposed to the archwire slot and which receive a small flexible wire for applying forces to the brackets to cause the diagonally opposed ends of the archwire slots to engage the upper and lower surfaces of a rectangular archwire to attain the predetermined torque value of the bracket.

The invention includes the use of tunnels or lumens for receiving small flexible wires to be activated while in the presence of the rectangular archwire which is retained in the rectangular archwire slots of the brackets. The tunnels are inclined relative to the rectangular archwire slots such that the small wire causes the application of forces to bring the diagonally opposed extremities of the archwire slots into contact with the upper and lower surfaces of the archwire to achieve the desired torque values.

While edgewise brackets having twin tie wings are illustrated in the drawings, it should be appreciated the invention is directed to edgewise brackets having any number of tie wings or configurations with a rectangular archwire slot that faces horizontally, and which are used to follow any of the many variations of edgewise and straight-wire techniques for straightening teeth. The conventional edgewise archwire slot configuration includes parallel directly opposed upper and lower walls extending perpendicular to a bottom or base wall. Some edgewise archwire slot configurations have upper and lower undulating walls with curvate edges or walls having multiple edges. Moreover, the invention can be incorporated in self-ligating brackets with or without tie wings. Further, it will be appreciated that the bracket may be made of any suitable material, such as metal, ceramic and plastic.

Referring now to the drawings, a bracket according to the invention and generally designated by the numeral 10, as shown in FIG. 1, represents an edgewise bracket for the upper right central incisor and which includes a bracket body 12 mounted on a base or pad 14. The bracket body comprises a pair of spaced apart tie wings 16, each having a pair of tie wing tips and which include a horizontally facing rectangular archwire slot 18 having upper and lower parallel walls and a perpendicular back wall. The archwire slot 18 is provided with a prescribed torque value in accordance with a selected prescription so that in maximum coaction with a rectangular archwire a desired torque of the tooth on which it is mounted will be attained.

Figure 2:
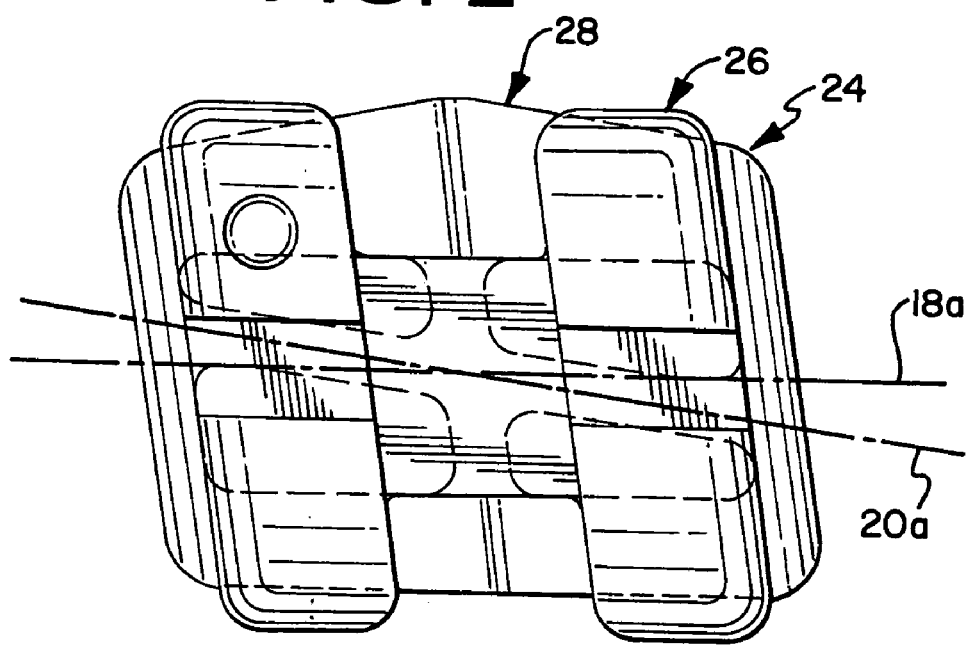
FIG. 2 is a front elevational view of an edgewise bracket according to the invention for use on an upper right central incisor of patient.

Behind or lingual to the archwire slot 18, the body includes a lumen or tunnel 20 for receiving a small flexible wire in the final stages of treatment to capture lost torque. The relationship between the archwire slot 18 and the tunnel 20 is such that the tunnel is vertically angularly related to the archwire slot as illustrated in FIG. 2 in the bracket 24 that is designed for an upper right central incisor tooth. This angular relation may be about 3 to 15 degrees, and preferably about 6 or 7 degrees. The axis 18a represents the axis of the archwire slot for the bracket in FIG. 2, while the axis 20a represents the axis for the lumen or tunnel 20.

The bracket (same bracket for upper right central) is provided with a prescription having appropriate tip and torque values. The bracket of FIG. 2 also is rhomboidal in shape from the buccolabial view to include a desired tip value.

As explained in the Background of the Invention, the manipulation of the edgewise or straight-wire mechanism has necessitated the manufacturing of the rectangular archwire slot and the rectangular archwire with vertical tolerances in sizes such that the archwire can be readily inserted into the archwire slot. Accordingly, the archwire becomes undersized for the slot and a play or tolerance exists between the two. It is this play or tolerance that must be dealt with in the final stages of orthodontic treatment in order to achieve the tip and torque values in a prescription. Most particularly, it is the torque value that needs the most capture in order to provide the ideal positions of the teeth when treatment is concluded. The operation of the bracket of the present invention to capture lost torque is illustrated in FIGS. 3 to 6.

Figure 5:
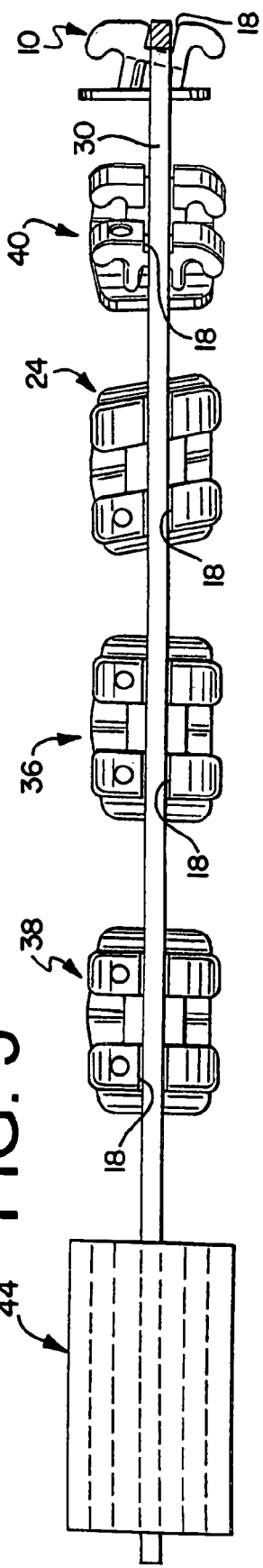
FIG. 5 is an elevational view of the upper right maxillary brackets for the upper right maxillary teeth with a rectangular archwire in place in the archwire slots and the ligatures omitted for clarity and illustrating in exaggerated form the spacing between the archwire and the upper and lower surfaces of the archwire slots.
Figure 6:
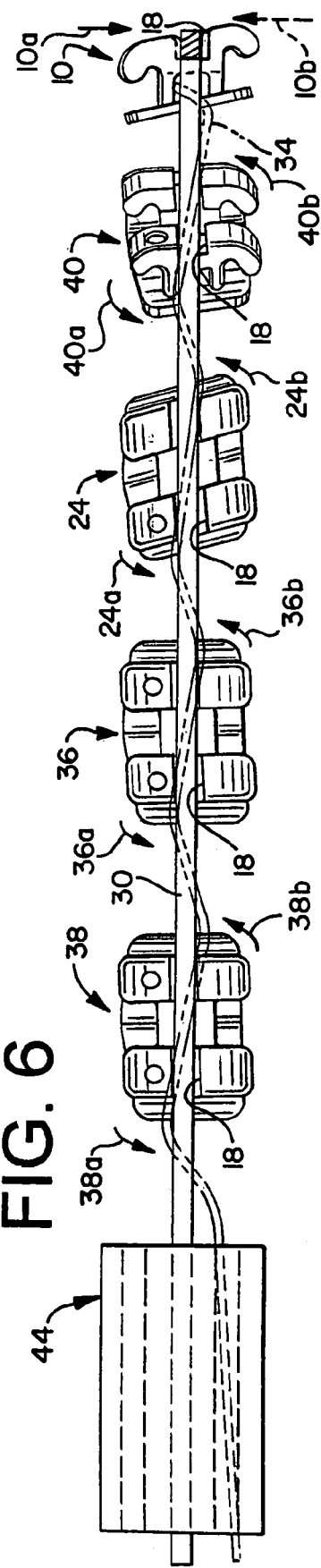
FIG. 6 is a view similar to FIG. 5 illustrating the use of a small flexible wire in the tunnels of the brackets in accordance with the invention and the final positioning of the brackets achieved by the capture of lost torque.

With respect to FIGS. 5 and 6, a rectangular archwire 30 is shown in the rectangular archwire slot 18 of the brackets. In FIG. 5 the archwire is shown in an imperfect torque control relationship with respect to the archwire slot such that the final positioning values of the tooth on which this bracket would be mounted cannot be attained, as seen most clearly at the central incisor 10. The invention includes the unique tunnel or lumen for receiving a small round flexible wire 34, as seen in FIG. 6, which applies a suitable force to the bracket and tooth on which it is mounted to cause the ends of the archwire slot of the bracket to square up with the archwire 30 as viewed from the mesial and distal to attain the full torque prescription value within the bracket.

FIGS. 5 and 6 show a system using premolar, canine, lateral and central incisor brackets of the invention. It will be appreciated that the bracket of the invention can be used with any number of brackets/teeth. While not shown, the main rectangular archwire 30 would be suitably retained in the archwire slots of the brackets. It also extends into an opening in the distally mounted buccal tube 44. It will be understood the buccal tubes would normally be mounted on molars to anchor the distal ends of the archwire and provide a reference for the archwire to align the teeth. The tube 44 includes a plurality of openings for receiving a plurality of wires. The openings may be round or rectangular in cross section depending upon the wire to be received. The rectangular archwire would normally fit into a rectangular opening of the tube. The buccal tube illustrated includes a central opening for the rectangular archwire and upper and lower openings that may either be round or rectangular in cross section. Depending upon the threading of the small flexible wire through the brackets, this wire would extend into and be anchored in one of the upper or lower openings.

Thus, the early stage of treatment would merely employ usage of the undersize rectangular archwire 30, as seen in FIG. 5, wherein the distal ends of the wire would be anchored in buccal tubes. Once the brackets/teeth are aligned with the archwire, the final stage of capturing lost torque will be implemented. At this stage of treatment, a small flexible wire is added to the system by threading the wire through the bracket lumens and into a buccal tube, as shown in FIG. 6.

Prior to the insertion and threading of the small flexible wire 34 in the tunnels or lumens of the brackets, the brackets and teeth on which they are mounted would generally take the positions shown in FIG. 5 where there is a slight clearance between the upper and lower surfaces of the archwire slots and the undersize archwire. Note the resulting lack of labio-lingual torque control of the central incisor 10.

In the final stages of treatment, the small flexible wire 34 will be threaded through the lumens of the brackets in such a way as to cause forces on the brackets so that the brackets capture lost torque. This wire will generally be anchored at its distal ends in a buccal tube 44. As seen in FIG. 6, the small flexible wire 34 threaded through the lumen applies a counterclockwise force to the brackets such that the diagonally opposed ends of the slots engage the archwire. This will cause the brackets to rotate about the long axis of the archwire and the diagonally opposed ends of the archwire slots to fully engage the archwire, resulting in the capturing of lost torque and attaining the torque values of the prescription. Depending on the needs of the patient, it will be appreciated the small flexible wire can be used to cause clockwise forces on the teeth to capture lost torque. In such brackets, the lumens would be angled in the opposite direction to those shown.

More particularly, as shown in FIG. 6, the small flexible wire enters the bracket 40 at a point slightly below the main archwire and exits the bracket at a point slightly above the main archwire and then downwardly to below the archwire at bracket 24 and upwardly and out the bracket 24 and downwardly into the bracket 36 and upwardly and out of the bracket 36 above the archwire and again downwardly into the tunnel of the bracket 38 and out of the tunnel above the archwire of the bracket 38 and then downwardly into the lower buccal tube opening of the buccal tube 44. As seen particularly in FIG. 2, with respect to the upper right arch, the small flexible wire would enter the lumen at one side of the bracket and exit the lumen at the other side. Pressure from the flexible wire at both entry and exit points of the lumen wall will first cause a counterclockwise rotational force to be applied to the bracket, and then a rotational force about the long axis of the archwire. It will be appreciated that depending upon the needs of the patient and location of the system in the mouth, the inclination of the lumens can be opposite to that which is shown in FIG. 2.

It should be appreciated that the brackets of the invention may optionally include vertical slots as shown in the bracket of FIGS. 1 and 2 for use with uprighting or rotating springs and other auxiliaries, although it is understood that lost torque is captured according to the invention without the need of using uprighting springs.

Figure 3:
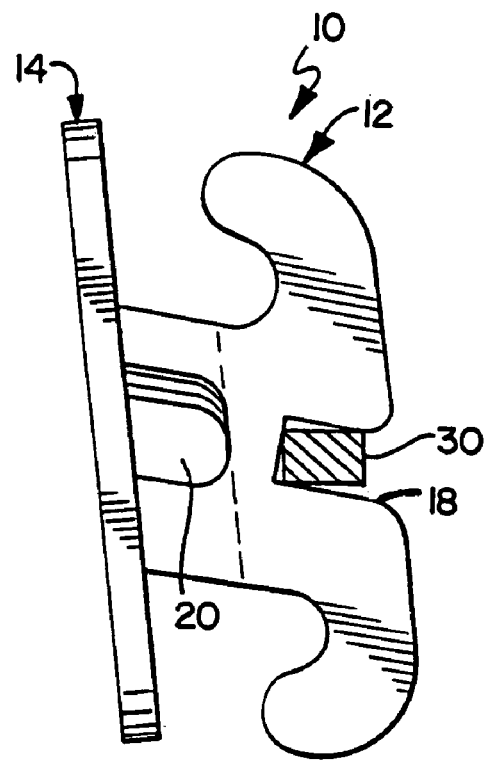
FIG. 3 is a side elevational view of the bracket of FIG. 1 and showing the position of the rectangular archwire in the rectangular archwire slot prior to the application of forces applied by a small flexible wire in the tunnel for capturing lost torque.
Figure 4:
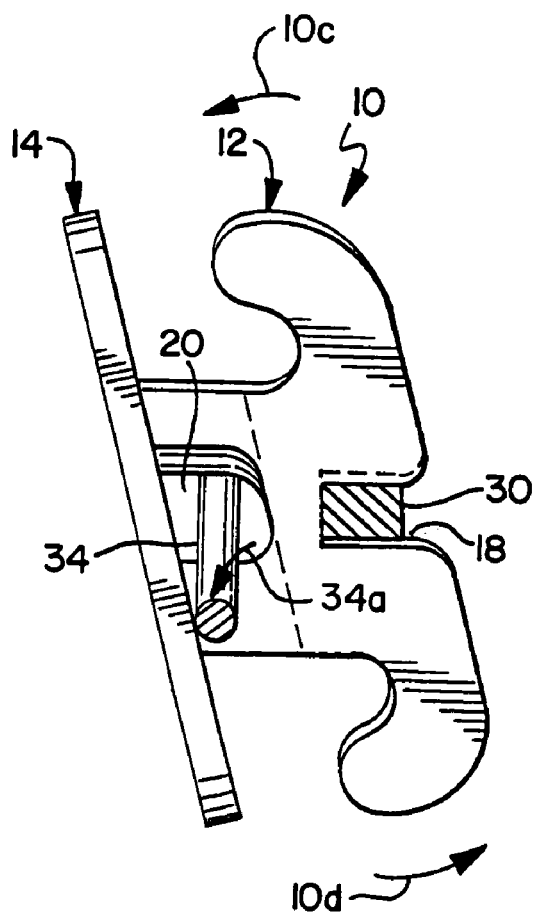
FIG. 4 is a view like FIG. 3 but also illustrating the use of a small flexible wire in the tunnel of the bracket and illustrating the capturing of lost torque occasioned by the vertical tolerances between the archwire and the slot.

In view of the foregoing, it will be appreciated that the invention includes the combination of an undersize rectangular archwire of any height and width in rectangular archwire slots of edgewise brackets and a small flexible wire threaded through tunnels angled such that a mesiodistal rotational force is placed on the brackets, as seen by the force arrows 38*a*, 38*b*, 36*a*, 24*a*, 24*b*, 40*a*, 40*b*, 10*a* and 10*b* in FIG. 6, causing the diagonally opposed outer ends of the archwire slot of each bracket to impinge on the upper and lower surfaces of the archwire. The force arrow 10*a* in solid is at the near or distal side of bracket 10, while the force arrow 10*b* in dotted is at the far or mesial side of the bracket. With respect to FIG. 4, a downward force is produced by the wire 34, as indicated by the force arrow 34*a*, that in respect to the position of the bracket 10 on the archwire, as seen in FIG. 3, causes torque movement or labiolingual rotation of the bracket about the archwire as depicted by force arrows 10*c* and 10*d*.

It will be understood that modifications and variations may be effected without departing from the scope of the novel concepts of the present invention, but it is understood that this application is to be limited only by the scope of the appended claims.

The invention claimed is:

1. An edgewise orthodontic bracket comprising,
    a horizontally opening archwire slot having directly opposed gingival and occlusal parallel means and, as viewed from the mesial or distal, defining a predetermined torque value and adapted to receive and coact with a main aligning rectangular archwire retained in said slot for controlling the directional movement of the bracket, an archwire coacting with said gingival and occlusal parallel means of said archwire slot, said archwire being slightly occlusogingivally undersized to said slot by at least 0.001 inch, and
    a mesiodistally extending tunnel or lumen separate from and occlusogingivally inclined to said archwire slot, said tunnel adapted to receive a relatively small flexible wire for applying a force to the bracket such as to cause diagonally opposed areas of the gingival and occlusal means of said slot to substantially engage the gingival and occlusal surfaces of the archwire to cause the bracket to rotate about the long axis of the archwire until the diagonally opposed areas of the slot engage and square up with the gingival and occlusal surfaces of the archwire.

2. The edgewise orthodontic bracket of claim 1, wherein said gingival and occlusal means defining a predetermined torque value includes gingival and occlusal parallel walls.

3. The edgewise orthodontic bracket of claim 1, wherein the bracket includes at least one tie wing.

4. The edgewise orthodontic bracket of claim 1, wherein the bracket includes a plurality of tie wings.

5. The edgewise orthodontic bracket of claim 1, wherein the bracket includes gingival and occlusal exterior surfaces parallel to each other, and the archwire slot is angled relative to the gingival and occlusal surfaces of the bracket.

6. The edgewise orthodontic bracket of claim 5, wherein the archwire slot is mesiodistally angled at least one degree from the gingival and occlusal surfaces of the bracket.

7. The edgewise orthodontic bracket of claim 5, wherein the archwire slot is mesiodistally angled one to five degrees to the gingival and occlusal surfaces of the bracket.

8. The edgewise orthodontic bracket of claim 1, wherein the tunnel or lumen is lingual to said archwire slot.

9. The edgewise orthodontic bracket of claim 1, which further includes a vertical slot for an uprighting spring.

10. The edgewise orthodontic bracket of claim 1, wherein the length of the lumen is substantially the same as the length of the archwire slot.

11. The edgewise orthodontic bracket of claim 1, wherein the length of the lumen is substantially longer than the length of the archwire slot.

12. An edgewise orthodontic bracket comprising,
a horizontally opening archwire slot having directly opposed gingival and occlusal parallel means and, as viewed from the mesial or distal, defining a predetermined torque value, a main aligning rectangular archwire retained in said slot for controlling directional movement, said archwire being slightly occlusogingivally undersized to said slot, and
a mesiodistally extending tunnel or lumen lingual to and separate from said slot extending angularly to said slot when viewing the bracket from the labial, said tunnel adapted to receive a relatively small flexible wire for applying a force to the bracket such as to cause diagonally opposed areas of the gingival and occlusal means of said slot to substantially engage the gingival and occlusal surfaces of the archwire to cause the bracket to rotate about the long axis of the archwire until the diagonally opposed areas of the slot engage and square up with the gingival and occlusal surfaces of the archwire.

13. The orthodontic bracket of claim 12, wherein said gingival and occlusal means defining a predetermined torque includes gingival and occlusal parallel walls.

14. An orthodontic system for applying corrective forces to teeth of an arch with brackets on central and lateral incisors, cuspids and bicuspids, each bracket including a horizontally opening rectangular archwire slot defining a predetermined torque value, a main aligning rectangular archwire retained in said slot for controlling the directional movement of the brackets, said archwire being slightly undersized occlusogingivally to said slots, and
each bracket including a mesiodistally extending tunnel or lumen occlusogingivally angled to and separate from the archwire slot, said tunnels adapted to receive a relatively small flexible wire for applying a force to said brackets such as to cause diagonally opposed ends of said slots to forcibly engage the gingival and occlusal surfaces of the archwire to cause the brackets to rotate about the long axis of the archwire until the diagonally opposed ends of the slots square up with the gingival and occlusal surfaces of the archwire.

15. The orthodontic system of claim 14, wherein the archwire slots of the brackets include gingival and occlusal walls defining a compensated tip value such that when the brackets have rotated both mesiodistally and labiolingually until the diagonally opposed surfaces of the gingival and occlusal walls have squared up with the gingival and occlusal surfaces of an undersize rectangular archwire substantially one hundred percent of both desired torque and tip values will be attained.

16. An edgewise orthodontic bracket for capturing lost torque of a prescription comprising,
a horizontally opening archwire slot having directly opposed parallel gingival and occlusal means defining a predetermined torque value, a main aligning rectangular archwire retained in said slot for controlling the directional movement of the bracket, said archwire being occlusogingivally undersized to permit the easy insertion of the archwire into the slot,
a mesiodistally extending tunnel or lumen lingual to and separate from said slot extending angularly to said slot when viewing the bracket from the labial, said tunnel adapted to receive a relatively small flexible wire for applying a force to the bracket such as to cause diagonally opposed areas of said slot to engage the gingival and occlusal surfaces of the archwire to cause the bracket to rotate about the long axis of the archwire and produce said predetermined torque value.

17. The bracket of claim 16, which further includes a plurality of tie wings.

18. The edgewise orthodontic bracket of claim 16, wherein said archwire slot is sized about 0.023 inch occlusogingivally and at least 0.028 inch labiolingually, and said archwire is sized 0.019 inch occlusogingivally and 0.028 inch labiolingually, wherein the labiolingual dimension of the archwire expedites the capture of lost torque.

19. In combination with an edgewise orthodontic bracket including a horizontally opening archwire slot sized about 0.023 inch occlusogingivally and at least 0.028 inch labiolingually, and an archwire occlusogingivally undersized to said slot by at least 0.001 inch,
a mesiodistally extending tunnel or lumen separate from and occlusogingivally inclined to said archwire slot for receiving a relatively small flexible archwire to apply a force to the bracket and square up the archwire slot to the archwire as viewed from the mesial and distal,
the improvement in the archwire size wherein the archwire is about 0.019 inch occlusogingivally and 0.028 inch labiolingually and greater labiolingually than conventional 0.019 inch high archwires, thereby reducing the time for capturing lost torque.

20. The orthodontic bracket of claim 1, wherein the bracket includes gingival and occlusal exterior surfaces parallel to the gingival and occlusal parallel means of the archwire slot, and parallel exterior mesial and distal surfaces at a compensated lesser tip angle to the archwire slot to provide the greater desired tip angle of the tooth when the diagonally opposed areas of the slot are squared up with the gingival and occlusal surfaces of the archwire.

21. The orthodontic bracket of claim 14, wherein the bracket includes gingival and occlusal exterior surfaces parallel to the archwire slot, and parallel exterior mesial and distal surfaces at a compensated tip angle to the archwire slot to provide the desired tip angle of the tooth when the diagonally opposed areas of the slot are squared up with the gingival and occlusal surfaces of the archwire.

22. The orthodontic bracket of claim 16, wherein the bracket includes gingival and occlusal exterior surfaces parallel to the gingival and occlusal parallel means of the archwire slot, and parallel exterior mesial and distal surfaces angled to the archwire slot to define a compensated tip angle to provide the desired tip angle of the tooth when the diagonally opposed areas of the slot are squared up with the gingival and occlusal surfaces of the archwire.

* * * * *